(12) United States Patent
Matthijs et al.

(10) Patent No.: US 6,420,602 B1
(45) Date of Patent: Jul. 16, 2002

(54) METHOD FOR THE PRODUCTION OF TETRAMETHYLTHIURAM DISULFIDE

(75) Inventors: Guido Matthijs, Gent; Patrick Christiaens, Waregem, both of (BE); August Van Gysel, Solre-le-Château (FR)

(73) Assignee: UCB, S.A., Brussels (BE)

( * ) Notice: Subject to any disclaimer, the term of this patent is extended or adjusted under 35 U.S.C. 154(b) by 0 days.

(21) Appl. No.: 09/890,398

(22) PCT Filed: Feb. 3, 2000

(86) PCT No.: PCT/EP00/00867
§ 371 (c)(1),
(2), (4) Date: Oct. 26, 2001

(87) PCT Pub. No.: WO00/46192
PCT Pub. Date: Aug. 10, 2000

(30) Foreign Application Priority Data

Feb. 3, 1999 (BE) ............................................. 9900071

(51) Int. Cl.$^7$ ...................... C07C 333/30; C07C 333/32

(52) U.S. Cl. ........................................................ 564/76
(58) Field of Search ............................................ 564/76

(56) References Cited

U.S. PATENT DOCUMENTS 4,459,424 A  7/1984 Eisenhuth et al. ............. 564/76
4,468,526 A * 8/1984 Eisenhuth et al. ............. 564/76

OTHER PUBLICATIONS

Patent Abstracts of Japan, vol. 014, No. 020 (C–676) (1990)—Abstract of JP 01–261361 A.

* cited by examiner

*Primary Examiner*—Peter O'Sullivan
(74) *Attorney, Agent, or Firm*—Wenderoth, Lind & Ponack, LLP

(57) ABSTRACT

The present invention relates to a novel method for the production of tetramethylthiuram disulfide, in which dimethylammonium dimethyldithiocarbamate is oxidized in aqueous solution with oxygen, in the presence of carbon disulfide and a lignosulfonate.

8 Claims, No Drawings

METHOD FOR THE PRODUCTION OF TETRAMETHYLTHIURAM DISULFIDE

This application is a 371 of PCT/EP00/00867, filed Feb. 3, 2000.

The present invention relates to a novel method for the production of tetramethylthiuram disulfide, in which dimethylammonium dimethyldithiocarbamate is oxidized in aqueous solution with oxygen, in the presence of carbon disulfide and a lignosulfonate.

Many methods for the production of tetramethylthiuram disulfide (the abbreviated term of TMTD will be used later in the whole description) have been described in the literature. In many of these methods, a dimethyldithiocarbamate salt is first of all prepared in aqueous solution by a reaction between dimethylamine and carbon disulfide in basic medium. The dimethyldithiocarbamate salt thus obtained is then oxidized to TMTD with various oxidants, for example hydrogen peroxide (patent DE 2,527,898), chlorine (U.S. Pat. No. 2,751,415 and U.S. Pat. No. 2,751,416), sodium nitrite (patent DE 1,164,394), and the like. A major disadvantage of most of these methods is that the formation of TMTD is accompanied by the formation of a salt from which it will have to be separated. A use must be found for the salt itself or it will have to be discharged.

Oxygen has more rarely been used as oxidant. Thus, patents FR 1,322,579 and FR 1,322,580 describe 2 very similar methods for the production of substituted thiuram disulfide, the first starting with alkali metal salts of substituted dithiocarbamic acids, the second starting with disubstituted secondary amines and carbon disulfide. In the 2 methods, the oxidation is produced by atmospheric oxygen in the presence of group VIII metal phthalocyanines as catalysts and the solvent may be water, the pH being maintained between 7 and 12. The yield of the first method reaches about 80% maximum, whereas it is limited to about 30% in the second.

In patent BE 892,143, there is described the synthesis of substituted thiuram disulfides by a method in which a disubstituted secondary amine whose pKa is at least 8 is reacted with carbon sulfide in the presence of oxygen or air as oxidant and a metal catalyst. The metals are chosen from cerium, manganese, copper, molybdenum, vanadium or one of their derivatives, and they are used in an amount of 0.01 to 5 millimoles per mole of secondary amine. The method is performed either in a single stage, or in 2 stages, the oxygen being used only in the second stage, and the intermediate dithiocarbamate being isolated or otherwise. The solvent preferably used as reaction medium is an aromatic hydrocarbon, a low-molecular weight alcohol or a mixture of the latter with water. In these organic solvents, the yield is practically quantitative and the products obtained generally possess sufficient purity for it not to be necessary to further purify them. By contrast, in pure water, the reaction is possible but it is much slower and the yield and selectivity are poorer, which constitutes a considerable disadvantage. According to this patent, it is possible to recycle the solvent with its catalyst more then 10 times, with no loss of yield or of catalytic activity. However, it is clear that at a certain moment, it will be necessary to separate the deactivated catalyst from the solvent and to purify the latter, which constitutes a disadvantage.

In patent BE 892,144, there is described a method which is essentially only distinguishable from that of patent BE 892,143 by the fact that ammonia or a tertiary amine is added to the reagents, and that the choice of catalytic metals is wider.

It would be of interest to have a method for the synthesis of TMTD in which:
the yields and selectivities would be practically quantitative;
the reaction medium would be water;
the oxidation would be performed with oxygen, or with a gas containing oxygen;
the formation of TMTD would not be accompanied by the formation of other products, such as salts.

In addition, for agrochemical applications:
the product obtained would be at a sufficiently high concentration in the reaction medium so that the latter can be directly spray-dried, without the need for filtration and washes giving mother liquors whose disposal or treatment would pose problems;
the products present in the reaction mixture would need to be compatible with an agrochemical use, without requiring prior separation (separation of the metal catalysts of patent BE 892,143 or of patents FR 1,322,579 and 1,322,580 for example).

It has been found, surprisingly, that all these combined objectives could be achieved by carrying out the oxidation of dimethylammonium dimethyldithio-carbamate (or DMDTC, a term used throughout this description) with oxygen, the pH being maintained between 7.0 and 8.0, in water and in the presence of a dispersing agent chosen from lignosulfonates.

Accordingly, the present invention relates to a method for the production of tetramethylthiuram disulfide (TMTD), in which dimethylammonium dimethyldithio carbamate (DMDTC) is oxidized in aqueous solution with oxygen, with addition of carbon disulfide, characterized in that the reaction is carried out in the presence of 0.5 to 25% of a lignosulfonate, calculated over the theoretical quantity of tetramethylthiuram disulfide (TMTD) which may be formed, and at a value of the pH of the reaction mixture of between 7.0 and 8.0.

Lignosulfonates are by-products derived from the treatment of paper pulp with sulfites (Ullmann's Encyclopedia of Industrial Chemistry, Vol. A15, pp. 305–315, VCH Ed., 5 ie. (1990)). Lignosulfonates are polymers based on phenyl propane units. As natural products, their composition varies according to the origin. They contain metals in trace form, in quantities well below the catalytic quantities used, for example, in patents BE 892,143, FR 1,322,579 or FR 1,322,580. Ligndsulfonates are very good dispersants, and that is why they are widely used in agrochemical formulations in the form of wettable powders or water-dispersible granules, to enhance the wettability and the dispersing qualities of active agents present in these formulations. They are marketed in the form of ammonium, sodium, calcium or magnesium salts and the like. By way of examples, there may be mentioned the products marketed under the trade names Wannin AM, Collex XM, Zewa SL, Borresperse NH, Zewakol MGN (all products from the company Borregaard-Lignotec), Novizel C12 (company Avebene), and the like. All these lignosulfonates are suitable for the aims of the present invention.

Normally, the lignosulfonates are used after the synthesis of the active agents, such as TMTD, during the preparation of the final formulations, with other additives. Unexpectedly, the surprising discovery has been made that the addition of these lignosulfonates during the stage of synthesis of active agents such as TMTD, through oxidation under an oxygen atmosphere of aqueous solutions of DMDTC, leads spontaneously to the formation of TMTD.

The DMDTC in aqueous solution, used as a reagent in the method for the production of TMTD according to the present invention, may be obtained by methods well known to persons skilled in the art, for example by reaction between dimethylamine in aqueous solution at 40% and carbon disulfide. Aqueous solutions containing about 55% by weight of DMDTC are easily obtained which are quite suitable as reagents according to the invention.

According to the invention, the lignosulfonate is used in quantities ranging from 0.5 to 25% by weight, relative to the weight of TMTD formed. The upper limit of this quantity is especially of interest in the case where the TMTD produced is intended for formulations of water dispersible granules for agrochemical uses. This quantity of lignosulfonate is such that it is no longer necessary to add more thereof during the formulation. However, it is not necessary to use such high quantities of lignosulfonates in order to obtain all the favorable effects of the present invention, and quantities of 0.5 to 3% by weight, relative to the weight of TMTD formed, are sufficient for this purpose.

The best results are obtained according to the invention if the oxidation of DMDTC is carried out at temperatures of between room temperature and 120° C., preferably between 50 and 90° C., and at pressure values of between 1 and 20 atmospheres, preferably 2 and 10 atmospheres. The pressure is maintained constant by addition of oxygen up to the end of the oxidation.

A good monitoring of the pH during the oxidation of DMDTC in aqueous solution is an important element in order to obtain a very high selectivity in relation to TMTD. Indeed, the oxidation of DMDTC releases dimethylamine according to the reaction scheme:

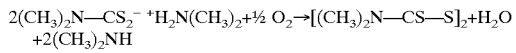

$$2(CH_3)_2N\text{---}CS_2^-\ ^+H_2N(CH_3)_2 + \tfrac{1}{2}\,O_2 \rightarrow [(CH_3)_2N\text{---}CS\text{---}S]_2 + H_2O + 2(CH_3)_2NH$$

Through gradual addition of carbon disulfide, the imethylamine released is converted to DMDTC, according to the reaction scheme:

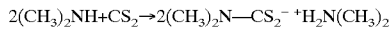

$$2(CH_3)_2NH + CS_2 \rightarrow 2(CH_3)_2N\text{---}CS_2^-\ ^+H_2N(CH_3)_2$$

This DMDTC is in turn oxidized to TMTD according to the first reaction.

If a transient excess of carbon disulfide is admitted during the oxidation, there are risks of inhibition of the oxidation, of agglomeration of the TMTD on the reactor surfaces and of explosion of the gaseous phase. If, on the other hand, an excessively low amount of carbon disulfide is admitted, there will be a transient excess of dimethylamine which will result in the formation of by-products and a loss of selectivity in relation to TMTD.

It is therefore important to admit into the oxidation reaction only the exact quantity of carbon disulfide necessary for its reaction with dimethylamine, as the latter is formed. The solution to this problem consists in automatically regulating the flow rate of carbon disulfide as a function of the pH continuously measured in the reaction mixture. Thus, by maintaining the pH at a value of between 7.0 and 8.0, a very good selectivity is obtained. Preferably, the pH is maintained between 7.0 and 7.3, which makes it possible to obtain a selectivity of close to 99.5% in relation to TMTD.

When the reaction mixture no longer absorbs oxygen, the reaction is complete. The last traces of carbon disulfide are removed by entrainment with nitrogen. If the TMTD formed is intended for agrochemical uses, the reaction mixture may be directly spray-dried, as it is, in order to provide TMTD which can be used as a fungicide.

Accordingly, the present invention also relates to a method for the production of tetramethylthiuram disulfide (TMTD) formulations, characterized in that:
 TMTD is produced according to the above mentioned method for the production of TMTD;
 the reaction mixture obtained according to the above mentioned method is directly spray-dried.

As a variant for agrochemical applications in the form of water dispersible granules, the reaction mixture containing the TMTD suspension may be ground to a sufficiently fine particle size, the customary ingredients such ask additional dispersing agents, wetting agents and inert fillers may be added thereto and the mixture may be granulated by spraying.

Accordingly, the present invention also relates to a method for the production of water dispersible granules containing tetramethylthiuram disulfide (TMTD), characterized in that:
 TMTD is produced according to the above mentioned method for the production of TMTD;
 the reaction mixture obtained according to the above mentioned method is ground;
 the customary ingredients for water dispersible granules are added thereto;
 the above mentioned mixture is granulated by spraying.

For other applications, for example in the vulcanization of rubber, the reaction mixture is treated in order to separate the TMTD from the lignosulfonate.

The method for the production of TMTD by oxidation, with oxygen, of DMDTC in aqueous solution, in the presence of lignosulfonates, according to the present invention, exhibits numerous advantages:
 the degree of conversion is practically quantitative, with TMTD yields greater than 98%, for a selectivity which may be up to 99.5%;
 the practically nonexistent formulation of by-products and the absence of added metal catalyst (in contrast to patents BE 892,143, FR 1,322,579 or FR 1,322,580) makes it possible to use the reaction mixture containing TMTD directly, without prior filtration, to make formulations thereof which can be used in agrochemistry. Filtration cakes and washing liquids are thus avoided, which makes the method economic and not harmful for the environment;
 the presence of lignosulfonates in the reaction mixture confers a dispersing and liquefying action on TMTD, which makes it possible to obtain a concentration as high as 40%, and even 45% at the end of the reaction. Without lignosulfonates, it is difficult to exceed a TMTD concentration of 30% in the reaction mixture, because adequate stirring of the TMTD suspension is no longer possible at this concentration. Such a high TMTD concentration facilitates the direct use of the reaction mixtures containing it in agrochemical formulations.

The method according to the invention may be carried out continuously, or in batches. In the latter case, it is possible, for example, to use a reactor withstanding pressure values of 20 atmospheres or more, comprising a stirrer of a type providing good contact between the liquid phase and the gaseous atmosphere above the liquid.

The reactor is first of all charged with an aqueous solution of DMDTC and there are then added the lignosulfonate and water in a quantity so as to obtain, at the end of the reaction, a suspension containing between 35 and 45% TMTD.

Oxygen is then added to a pressure of 1 to 20 atmospheres.

The contents of the reactor are then heated to a sufficiently high temperature to initiate the oxidation reaction.

The temperature is maintained at a fixed value (between room temperature and 120° C.) by cooling the reactor.

The initial pressure is maintained by constant addition of oxygen, regulated with a pressure regulator.

The pH of the reaction mixture is maintained between 7.0 and 8.0 by continuous addition of carbon disulfide, regulated by a control valve controlled by a pH-stat signal.

The reaction is stopped when the consumption of oxygen and of carbon disulfide stops.

The reactor is then emptied and the last traces of carbon disulfide are removed by entrainment by means of a nitrogen stream.

The aqueous suspension of TMTD is then spray-dried in a drier, such as for example a spray-drier, a fluidized bed or a "flash-drier".

The following examples illustrate the invention without however limiting it.

EXAMPLE 1

The following are introduced into a 1.2 liter stainless steel, pressure-resistant reactor equipped with a heating or cooling jacket, a Pt-100 resistivity thermometer, a tube for supplying carbon disulfide comprising a piston pump controlled by an electrode for measuring the pH of the reaction mixture, a tube for supplying oxygen, a manometer and a stirrer:

450 g of a 55.05% aqueous solution of DMDTC (1.49 moles);

7.2 g of Borresperse NH (a lignosulfonate in ammonium form), that is 2% of the quantity of TMTD which it is theoretically possible to obtain;

250 ml of water.

The pH is maintained constant at 7.2 during the whole reaction by automatic addition of carbon disulfide according to this pH value.

The reactor temperature is brought to 80° C. and oxygen is added until a pressure of 4 atmospheres is obtained. The oxygen consumption starts as soon as it is added and the pressure is kept constant by continuous addition of oxygen. The oxygen consumption is determined by means of a flow meter. As soon as the oxygen consumption starts, carbon disulfide is admitted into the reactor. After 115 minutes, the reaction stops. 114 g of carbon disulfide were consumed, that is 1.497 moles.

After filtration, washing of the filtration cake and drying, 354 g of TMTD are obtained, that is a yield of 98.8% relative to the theoretical value. The product has a melting point of 153.2° C.

EXAMPLE 2 (comparative)

The procedure is carried out as in Example 1, with the same quantities of reagents, at the same concentrations and in the same apparatus, omitting however to control the operation of the piston pump delivering the carbon disulfide to the electrode measuring the pH of the reaction mixture. By contrast, carbon disulfide is added to the reactor by manually regulating the capacity of the pump, by gradually reducing the capacity as the oxygen is consumed in the reaction. By carrying out the procedure in this manner, 116 g of carbon disulfide (1.523 moles) are added over a period of about 90 minutes, while the consumption of oxygen stops after 110 minutes.

335 g of TMTD (1.393 moles) are thus obtained, which represents a yield of 93.5%. The product has a melting point of 153° C.

This example shows that a poor synchronization between the addition of carbon disulfide and oxygen (which determines the appearance of dimethylamine) causes a reduction in the yield of TMTD obtained.

EXAMPLES 3 to 5 (according to the invention) AND 6 AND 7 (comparative)

These examples show the influence of the pH on the selectivity of the reaction.

These examples are carried out under conditions identical to those of Example 1, except that the pH was set at 5 different values. Table I indicates successively the example No., the applied pH, the duration of the reaction, the rate of conversion of DMDTC, the selectivity in relation to TMTD and the yield obtained in relation to TMTD.

TABLE I

| Example | pH | Duration | Conversion | Selectivity | Yield |
| --- | --- | --- | --- | --- | --- |
| 3 | 7.2 | 115' | 99.5% | 99.6% | 99.1% |
| 4 | 7.5 | 110' | 99.2% | 99.0% | 98.2% |
| 5 | 8.0 | 100' | 99.4% | 98.0% | 97.4% |
| 6 | 8.5 | 100' | 99.5% | 93.0% | 92.5% |
| 7 | 9.0 | 95' | 99.5% | 73.0% | 72.6% |

These examples show that the selectivity and yields in relation to TMTD are low or poor for pH values of 8.5 and 9.0, whereas they are good for pH values of 8.0 to 7.2, and even practically quantitative for this last value, at the expense of a duration of reaction which is barely longer.

EXAMPLES 8 TO 13

These examples are carried out under conditions identical to those of Example 1, except that the nature of the lignosulfonate is different from one example to another, its quantityostill being 2% by weight relative to the weight of TMTD which it is theoretically possible to obtain. Table II indicates the results obtained Table II indicates successively the example No., the trade name and the type of lignosulfonate used, the duration of the reaction and the yield obtained in relation to TMTD.

TABLE II

| | Lignosulfonate | | | |
| --- | --- | --- | --- | --- |
| Example | Trade name | Type | Duration | Yield |
| 8 | Borresperse NH | Ammonium | 120' | 98.8% |
| 9 | Wannin AM | Ammonium | 125' | 99.1% |
| 10 | Collex XM | Calcium | 115' | 98.7% |
| 11 | Zewakol MGN | Magnesium | 110' | 99.2% |
| 12 | Zewal SL | Sodium | 200' | 98.2% |
| 13 | Novizel C12 | Calcium | 180' | 99.0% |

This table shows that the yield obtained in relation to TMTD is still very good, greater than 98.0%, regardless of the lignosulfonate used. Slight differences are simply observed in the rate of the reaction as a function of the lignosulfonate used.

EXAMPLES 16 (according to the invention) AND 17 AND 18 (comparative)

These examples show the effects obtained with a lignosulfonate, compared with those obtained with a synthetic dispersant and without any additive.

These 3 examples are carried out in an identical manner to Example 1, with however a reaction time of 5 hours and the following sole differences:

in Example 16, 3.6 g of Zewa SL are used as lignosulfonate (1%, of the theoretical quantity of TMTD which it is possible to obtain), instead of 2% Borresperse NH;

in Example 17, 3.6 g (1% over TMTD) of Supragil GN are used, the trade name of an anionic dispersant which is a synthetic sodium phenylsulfonate (marketed by the company Rhône-Poulenc Geronazzo);

in Example 18, no additive is used.

Table III gives the results obtained. This Table III indicates successively the example No., the nature of the additive, the rate of conversion of DMDTC, the selectivity and the yield in relation to TMTD.

TABLE III

| Example | Additive | Conversion | Selectivity | Yield |
|---|---|---|---|---|
| 16 | Zewa SL | 99.5% | 99.6% | 99.1% |
| 17 | Supragil CN | 27.0% | 99.7% | 26.9% |
| 18 | — | 26.2% | 99.7% | 26.1% |

As can be observed on reading this table, in the absence of additive, the reaction is extremely slow.

The same applies in the presence of a synthetic dispersant, whereas excellent results are obtained with a lignosulfonate according to the invention.

EXAMPLE 19

The following are introduced into a 100 liter stainless steel reactor equipped as in Example 1:

40 kg of an aqueous solution of DMDTC at 55.6% by weight (133.73 moles);

643 g of Wannin AM (ammonium lignosulfonate), that is 2% of the theoretical quantity of TMTD which it is possible to obtain;

27.5 liters of demineralized water.

The content of the reactor is stirred and heated to 60° C., at a constant oxygen pressure of 4 atmospheres. As soon as the consumption of oxygen begins, the temperature rises rapidly to 80° C. This temperature is maintained constant during the whole reaction by circulating water in the cooling jacket. The oxygen consumption is determined by means of a flowmeter. An electrode for measuring the pH is immersed in the reaction mixture and regulates the rate of addition of carbon disulfide by means of a piston pump. The oxygen consumption stops after 145 minutes. The total quantity of carbon disulfide added is 10.190 kg (133.83 moles). After removing the residual traces of carbon disulfide by means of a nitrogen stream, 79.72 kg of suspension containing 39.9% by weight of TMTD are obtained.

The TMTD yield is 31.8 kg, that is 98.9% of the theoretical value.

EXAMPLE 20

The procedure is carried out as in Example 19, using however only 322 g of Wannin AM, that is 1% of the theoretical quantity of TMTD which may form, instead of 2% in Example 19. The oxygen consumption stops after 195 minutes and a total of 10.185 kg of carbon disulfide was added (133.76 moles). After removing the residual traces of carbon disulfide by means of a nitrogen stream, 79.72 kg of a suspension of TMTD at 40% by weight are obtained.

The TMTD yield is 31.75 kg, that is 98.75% of the theoretical value.

The suspension as obtained is spray-dried in a pilot spray-drier to give a final product containing 98.5% TMTD, which can be used in wettable powder formulations intended for agriculture.

EXAMPLE 21

The procedure is carried out exactly as in Example 19. The oxygen consumption stops after 150 minutes and a total of 10.189 kg of carbon disulfide was added (133.82 moles). After removing residual traces of carbon disulfide by means of a nitrogen stream, 79.5 kg of a suspension of TMTD at 40.1% by weight are obtained.

The TMTD yield is 31.88 kg, that is 99.2% of the theoretical value.

The suspension as obtained is ground in a ball mill until a mean particle size of about 4 micrometers is obtained. Dispersing agents, wetting agents and inert fillers are added thereto until a solid matter content of 81% is obtained. The suspension is spray-dried to give water dispersible granules having the same characteristics as those obtained by a conventional method, such as the one described in patent BE 830,547.

TMTD content: 81.5%;
Moisture content: 1.5%;
Suspendibility (CIPAC MT 168): 89%
Wettability (CIPAC MT 53.31): 10 seconds;
Wet sieving residue (CIPAC MT 167):
at 125 micrometers: 0.01;
at 75 micrometers: 0.06%.

What is claimed is:

1. A method for the production of tetramethylthiuram disulfide (TMTD), in which dimethylammonium dimethyldithiocarbamate (DMDTC) is oxidized in aqueous solution with oxygen, with addition of carbon disulfide, characterized in that the reaction is carried out in the presence of 0.5 to 25% of a lignosulfonate, calculated over the theoretical quantity of tetramethylthiuram disulfide (TMTD) which may be formed, and at a value of the pH of the reaction mixture of between 7.0 and 8.0.

2. The method as claimed in claim 1, characterized in that the lignosulfonate is used in an amount of 0.5 to 3%, calculated over the theoretical quantity of tetramethylthiuram disulfide which may form, and in that it is chosen from ammonium, sodium, calcium and magnesium lignosulfonates.

3. The method as claimed in claim 1, characterized in that the reaction is carried out at a temperature of between room temperature and 120° C. and at a pressure of between 1 and 20 atmospheres.

4. The method as claimed in claim 1, characterized in that the reaction is carried out at a temperature of between 50 and 90° C. and at a pressure of between 2 and 10 atmospheres.

5. The method as claimed in claim 1, characterized in that the reaction is carried out at a value of the pH of the reaction mixture of between 7.0 and 7.3.

6. The method as claimed in claim 1, characterized in that the quantity of carbon disulfide admitted into the reactor is determined by the value of the pH.

7. A method for the production of tetramethylthiuram disulfide formulations, characterized in that:

tetramethylthiuram disulfide is produced as claimed in claim 1 and the reaction mixture obtained according to the above mentioned method is directly spray-dried.

8. A method for the production of water dispersible granules containing tetramethylthiuram disulfide, characterized in that:

tetramethylthiuram disulfide is produced as claimed in claim 1;

the reaction mixture obtained according to the above mentioned method is ground, the customary ingredients for water dispersible granules are added thereto, and the above mentioned mixture is granulated by spraying.

\* \* \* \* \*